United States Patent [19]
Takahashi et al.

[11] Patent Number: 5,951,464
[45] Date of Patent: Sep. 14, 1999

[54] DISTAL END PART OF ENDOSCOPE

[75] Inventors: Nagashige Takahashi; Hiromichi Shibuya, both of Tokyo, Japan

[73] Assignee: Asahi Kogaku Kogyo Kabushiki Kaisha, Tokyo, Japan

[21] Appl. No.: 08/424,115

[22] Filed: Apr. 19, 1995

Related U.S. Application Data

[63] Continuation of application No. 07/893,044, Jun. 3, 1992, abandoned.

[30] Foreign Application Priority Data

Jun. 5, 1991 [JP] Japan ................................ 3-232573

[51] Int. Cl.$^6$ ........................................................ A61B 1/06
[52] U.S. Cl. ........................ 600/176; 600/127; 600/129; 600/121; 600/160; 600/169; 600/181
[58] Field of Search ..................................... 600/127, 129, 600/121, 160, 175, 176, 177, 169, 181, 106; 359/601, 613, 385

[56] References Cited

U.S. PATENT DOCUMENTS

| | | |
|---|---|---|
| 4,419,987 | 12/1983 | Ogiu .................................... 600/106 X |
| 4,639,837 | 1/1987 | Yokota ................................. 385/115 X |
| 4,697,577 | 10/1987 | Forkner ........................................ 128/6 |
| 4,747,661 | 5/1988 | Ohkuma .................................. 128/6 X |
| 4,779,613 | 10/1988 | Hashiguchi et al. ........................ 128/6 |
| 4,809,678 | 3/1989 | Klein ........................................... 128/4 |
| 4,867,546 | 9/1989 | Nishioka et al. . |
| 4,929,070 | 5/1990 | Yokota et al. ............................ 600/177 |
| 4,998,182 | 3/1991 | Krauter et al. ............................ 128/6 X |
| 5,150,702 | 9/1992 | Miyanaga et al. ....................... 600/181 |
| 5,257,617 | 11/1993 | Takahashi . |
| 5,278,642 | 1/1994 | Danna et al. ........................ 600/181 X |
| 5,359,991 | 11/1994 | Takahashi et al. . |

Primary Examiner—Beverly M. Flanagan
Attorney, Agent, or Firm—Greenblum & Bernstein, P.L.C.

[57] ABSTRACT

A distal end part of an endoscope having a viewing window for introducing light from an object into an objective optical system for forming an observed image. An illuminating window is disposed in a side by a side relationship with the viewing window for illuminating a visual field of the objective optical system. A continuous transparent cover covers the surfaces of both the illuminating and viewing windows. A window glass is attached to the viewing window in such a manner that a virtual image of the outer edge portion of the window glass, which is produced by single reflection from the inner side of the outer surface of the transparent cover, lies outside the visual filed of the objective optical system.

8 Claims, 5 Drawing Sheets

DISTAL END PART OF ENDOSCOPE

This application is a continuation of application Ser. No. 07/893,044, filed Jun. 3, 1992, now abandoned.

BACKGROUND OF THE INVENTION

The present disclosure relates to subject matter contained in Japanese Patent Application No. 3-232573 (filed on Jun. 5, 1991), which is expressly incorporated herein by reference in its entirety.

1. Field of the Invention

The present invention relates to a distal end part of an endoscope in which the surfaces of illuminating and viewing windows, which are provided in a side by side in the distal end of an insert part of the endoscope, are covered with a transparent cover.

2. Description of the Prior Art

FIG. 4 shows the distal end part of an endoscope according to a prior art. Reference numeral 51 denotes a distal end block that is provided at the distal end of an insert part of the endoscope. A continuous transparent cover 52 is provided at the distal end of a sheath for removably covering the insert part of the endoscope.

Illuminating light, that is emitted from an illuminating window 53 provided in the distal end block 51, passes through the transparent cover 52 and illuminates an object. Light reflected from the object enters an objective optical system 54a through a viewing window 54, so that an image of the object is formed on an entrance end face 55a of an image guide fiber bundle 55.

However, if the illuminating and viewing windows 53 and 54, which are disposed in a side by side, are covered with the transparent cover 52, part of the illuminating light emitted from the illuminating window 53 is reflected at the inner side of the surface of the transparent cover 52 and thus transmitted therethrough, as shown in FIG. 5. The transmitted light shines brightly on the chamfered portion or edge portion of the outer edge portion 57 of a window glass 56 provided in the viewing window 54.

Consequently, light from the brightened outer edge portion 57 of the window glass 56 is further reflected at the inner side of the surface of the transparent cover 52 and enters the visual field of the objective optical system 54a, thus producing an adverse effect on the observed image. In other words, since the virtual images 56a and 57a of the window glass 56 and its outer edge portion 57, which are produced by reflection, are formed within the visual field A, as shown by the chain line in FIG. 5, the bright virtual image 57a of the outer edge portion 57 is undesirably observed.

SUMMARY OF THE INVENTION

An object of the present invention is to provide a distal end part of an endoscope which is designed so that, even if the surfaces of the illuminating and viewing windows, which are disposed in a side by side, are covered with a continuous transparent cover, light reflected at the inner side of the surface of the transparent cover has no adverse effect on the observed image.

Other objects and advantages of the present invention will become apparent from the following detailed description of an illustrated embodiment of the invention.

According to the present invention, there is provided a distal end part of an endoscope, including: a viewing window for introducing light from an object into an objective optical system for forming an observed image; and an illuminating window disposed in a side by side with the viewing window for illuminating a visual field of the objective optical system. The distal end part further includes a continuous transparent cover for covering the surfaces of both the illuminating and viewing windows; and a window glass that is attached to the viewing window in such a manner that a virtual image of the outer edge portion of the window glass, which is produced by single reflection from the inner side of the outer surface of the transparent cover, lies outside the visual field of the objective optical system.

BRIEF DESCRIPTION OF THE DRAWINGS

The present invention may be more fully understood from the description of a preferred embodiment of the invention set forth below, together with the accompanying drawings, in which.

DESCRIPTION OF THE EMBODIMENT

One embodiment of the present invention will be described below with reference to the accompanying drawings.

Figure 1:
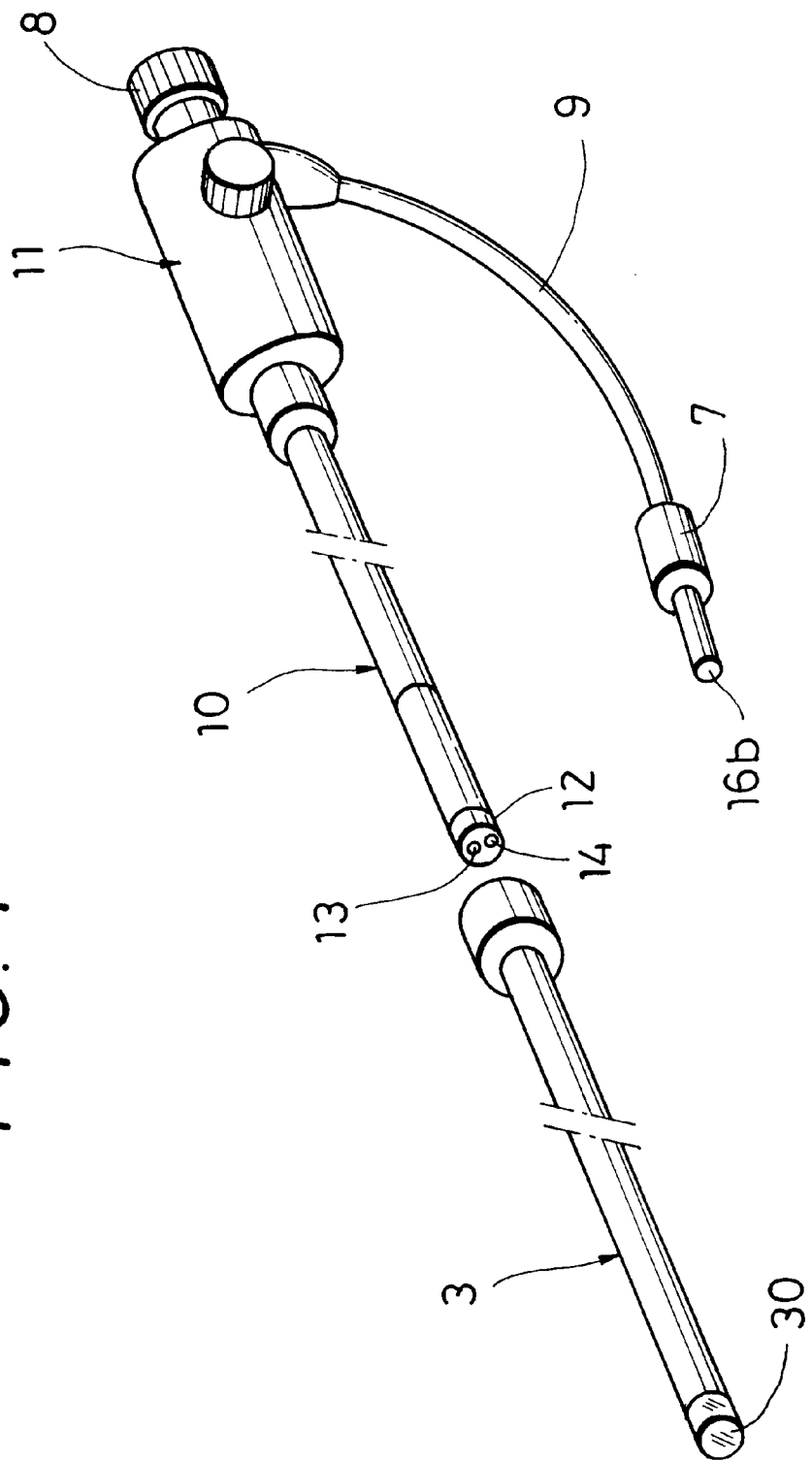
FIG. 1 is a perspective view of one embodiment of an endoscope according to the present invention.

Referring to FIG. 1, a distal end block 12 is connected to the distal end of a flexible, long and narrow insert part 10. The forward end face of the distal end block 12 is provided with an illuminating window 13, for emitting illuminating light, and a viewing window 14, for introducing an optical image into an objective optical system. The windows 13 and 14 are disposed in a side by side relationship facing forwardly. Thus, the observation field of view is illuminated with illuminating light emitted from the illuminating window 13.

Reference numeral 11 denotes a control part, and reference numeral 8 an eyepiece. A flexible connecting tube 9 is connected to the control part 11. A light guide connector 7, which is connected to a light source apparatus (not shown), is attached to the distal end of the tube 9. An entrance end face 16b of a light guide fiber bundle 16 (shown in FIG. 3) is disposed at the projecting end of the connector 7.

A flexible sheath 3 can be removably fitted over the insert part 10 of the endoscope. A transparent cover 30 is connected to the distal end of the sheath 3 in such a manner that no water will leak in through the joint of the cover 30 and the sheath 3. The cover 30 is formed of a transparent plastics material, e.g., acrylic plastics. Accordingly, only the sheath 3, with the transparent cover 30, can be disposed each time the endoscope has been used, thus enabling the endoscope to be used hygienically.

Figure 2:
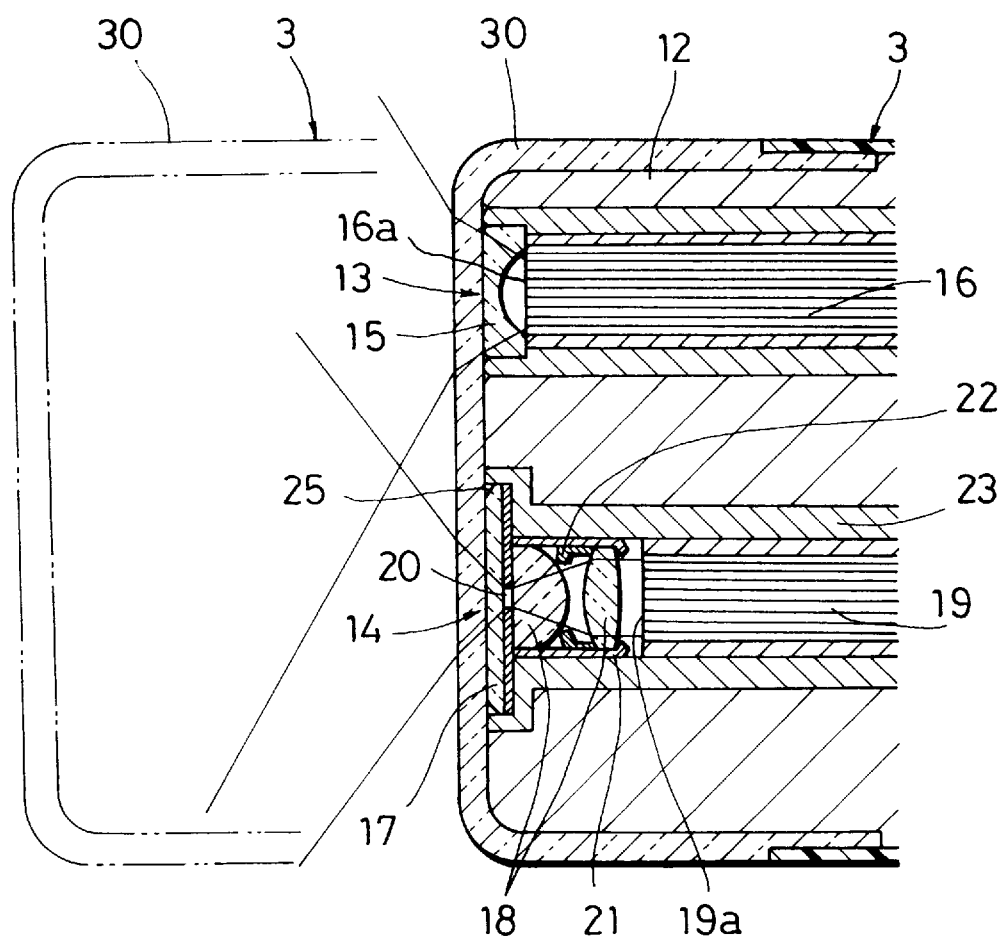
FIG. 2 is a sectional side view of the embodiment of the present invention.

FIG. 2 shows the distal end portion of the insert part 10, which is covered with the sheath 3.

A concave lens 15 is fitted into the illuminating window 13. An exit end face 16a of the light guide fiber bundle 16 is disposed in the rear of the concave lens 15. In addition, a plane-parallel disk-shaped window glass 17 is fitted into the viewing window 14, and an objective lens 18 is disposed in the rear of the window glass 17 so that an observed image is formed on an entrance end face 19a of an image guide fiber bundle 19. It should be noted that the window glass 17 may be a lens that constitutes a part of the objective lens 18.

The window glass 17 is formed with a relatively large diameter so that a virtual image of the circular beveled or chamfered outer edge portion 25 of the window glass 17, which is produced by single reflection from the inner side of the outer surface of the transparent cover 30, lies outside the visual field defined by the objective lens 18 and the image guide fiber bundle 19.

Figure 3:
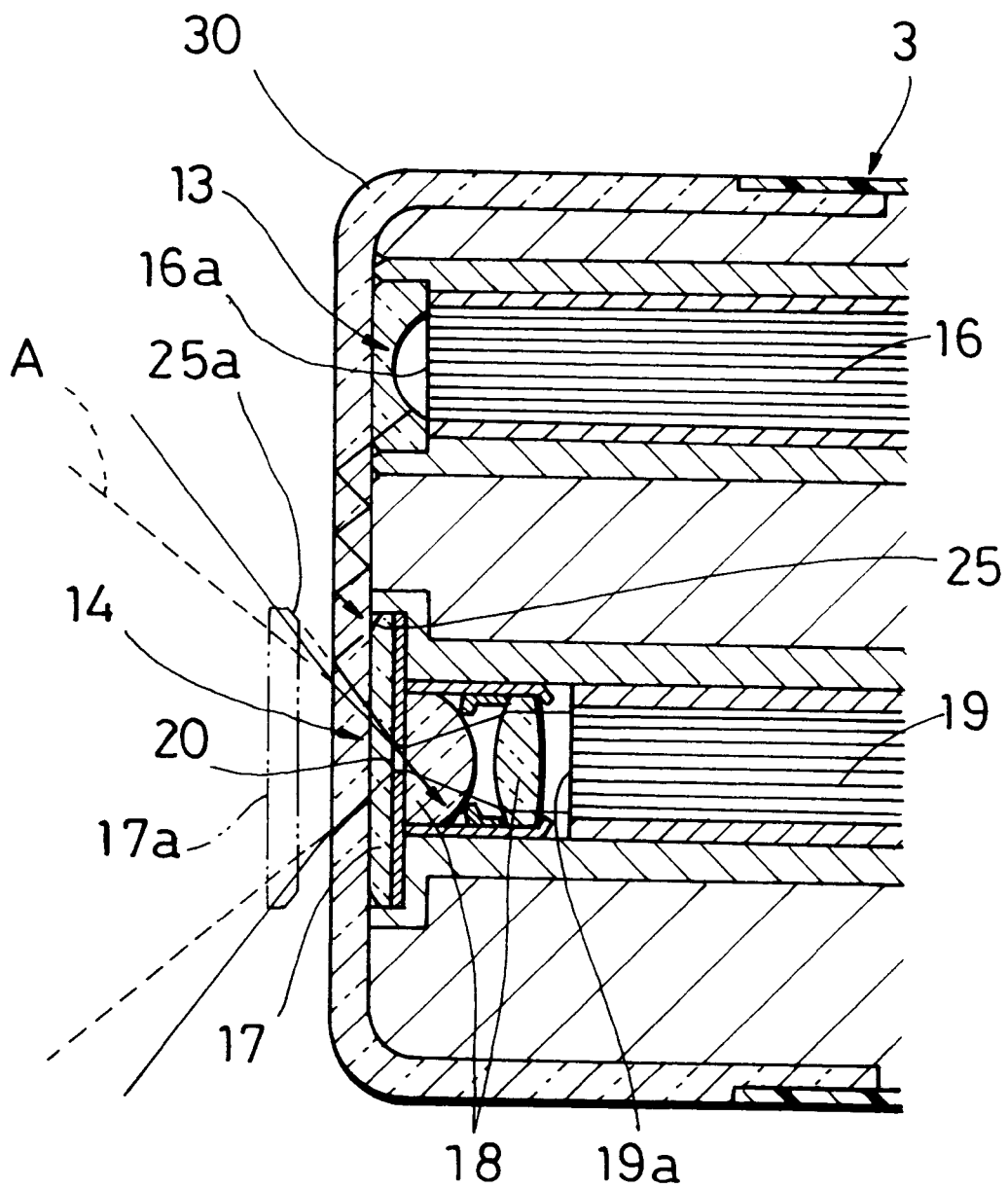
FIG. 3 is a sectional side view of the embodiment of the present invention.
Figure 4:
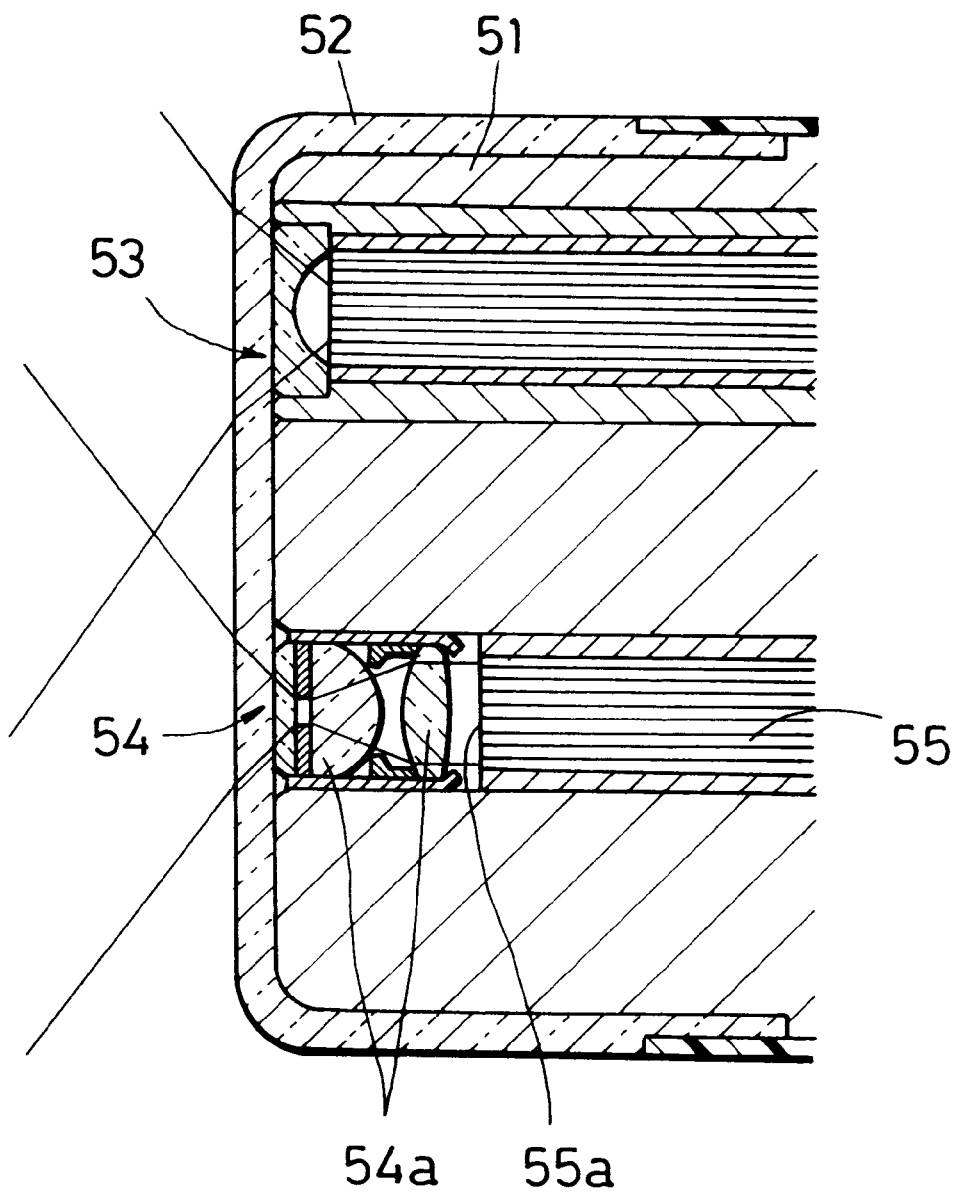
FIG. 4 is a sectional side view of the distal end part of an endoscope according to a prior art.
Figure 5:
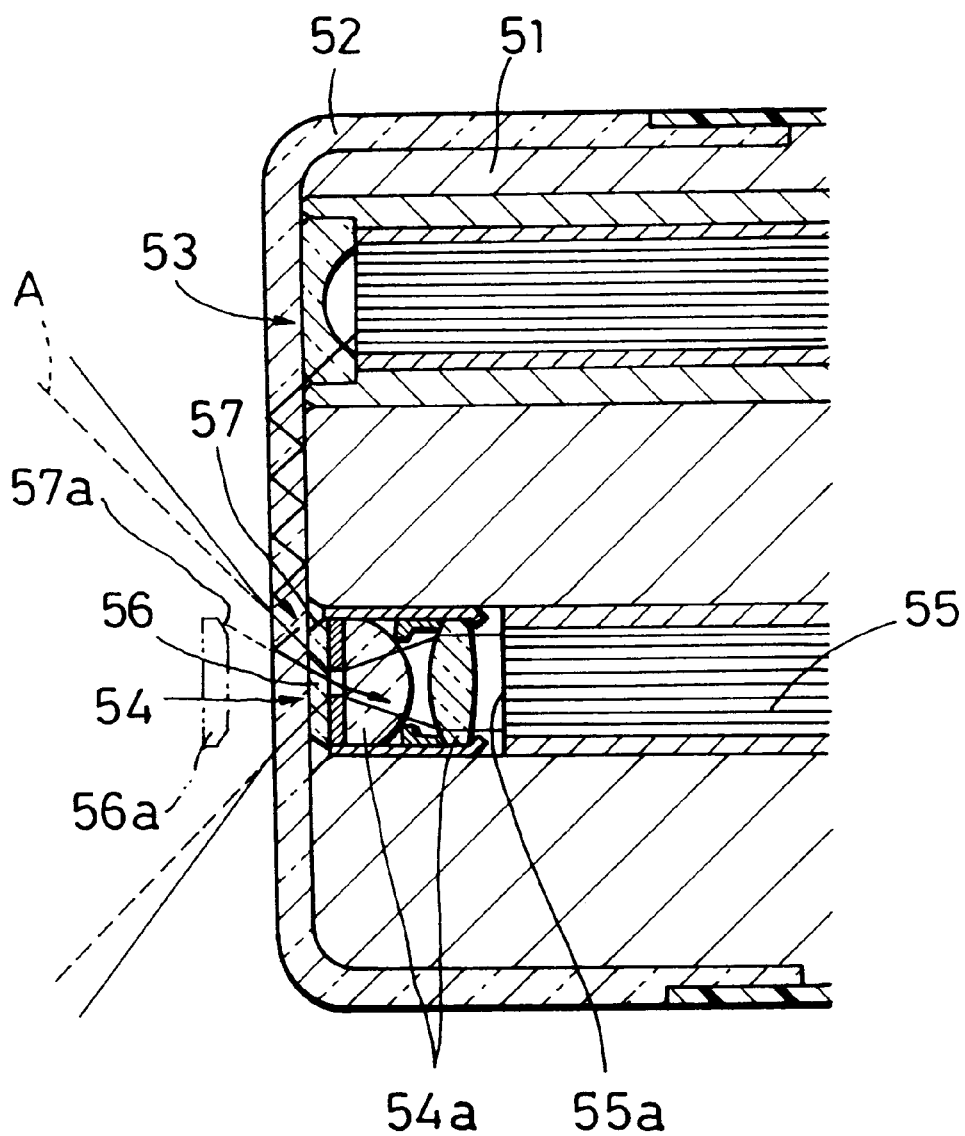
FIG. 5 is a sectional side view of the prior art, as shown in FIG. 4.

More specifically, reference numerals 17a and 25a in FIG. 3 denote virtual images of the window glass 17 and its outer edge portion 25. The virtual image 25a of the outer edge portion 25 lies outside the visual field A, as shown by the chain line.

Referring to FIG. 2, reference numeral 20 denotes an aperture diaphragm, and 21 a lens frame. A spacer 22 is disposed inside the objective lens 18. In addition, a support tube 23, which retains the parts inside the viewing window 14 and the image guide fiber bundle 19, is secured to the distal end block 12.

In FIG. 2, the flexible sheath 3, which is drawn outwardly and forwardly of the insert part, is shown by the two-dot chain line. When the insert part of the endoscope is inserted into the sheath 3 fully, both the concave lens 15 in the illuminating window 13 and the window glass 17 in the viewing window 14 are closely contacted and covered with the transparent cover 30, which is a continuous member. Accordingly, no substantial reflection occurs at the boundary between the surface of the concave lens 15 or the surface of the window glass 17 and the reverse surface of the transparent cover 30.

In the distal end part of the endoscope, arranged as described above, illuminating light, that is emitted forwardly through the illuminating window 13 from the exit end face 16a of the light guide fiber bundle 16, passes through the transparent cover 30 and illuminates the object. Reflected light from the object passes through the viewing window 14. An image of the object is formed on the entrance end face 19a of the image guide fiber bundle 19 by the objective lens 18.

However, part of the illuminating light from the illuminating window 13 reaches the window glass 17 after being repeatedly reflected at the inner sides of the surfaces of the transparent cover 30, and illuminates the outer edge portion 25 of the window glass 17, as shown in FIG. 3. As a result, the outer edge portion 25 of the window glass 17 shines brightly.

Then, light emitted from the brightened outer edge portion 25 is further reflected at the inner side of the outer surface of the transparent cover 30. The reflected light enters the objective lens 18 through the diaphragm 20.

However, the virtual image 25a of the outer edge portion 25 of the window glass 17, which is produced by single reflection from the inner side of the outer surface of the transparent cover 30, lies outside the visual field A, as shown by the chain line in FIG. 3. Accordingly, even if the light that is emitted from the outer edge portion 25 of the window glass 17 and reflected once at the inner side of the outer surface of the transparent cover 30 enters the objective lens 18, it will not reach the entrance end face 19a of the image guide fiber bundle 19. Hence it will not appear in the observed image.

It should be noted that since the image of the brightened outer edge portion 25 of the window glass 17 is repeatedly reflected at the inner sides of the surfaces of the transparent cover 30, light, that is reflected a plurality of times, also enters the objective lens 18 through the diaphragm 20. However, the reflectivity at the inner side of the surface of the transparent cover 30 is, for example, about 4. Therefore, the light reflected a plurality of times is much lower in terms of brightness than that of the light reflected once and hence has substantially no adverse effect on the observed image.

It should also be noted that the present invention may also be applied to a video endoscope that employs a solid-state imaging device in place of the image guide fiber bundle 19.

According to the present invention, a virtual image of the outer edge portion of the window glass provided in the viewing window, which is produced by single reflection from the inner side of the outer surface of the transparent cover, lies outside the visual field of the objective optical system. Accordingly, even if the outer edge portion of the window glass is illuminated to shine brightly with illuminating light that is transmitted from the illuminating window by being reflected inside the transparent cover, light from the brightened outer edge portion will have no adverse effect on the observed image, so that it is possible to obtain an observed image of good quality.

While the invention has been described by reference to a specific embodiment chosen for purposes of illustration, it should be apparent that numerous modifications could be made thereto by those skilled in the art without departing from the basic concept and scope of the invention.

We claim:

1. A distal end part of an endoscope, comprising:

a viewing window for introducing light from an object into an objective optical system having a visual field for forming an observed image;

an illumination window disposed in a side by side relationship with said viewing window for illuminating said visual field of said objective optical system;

a continuous transparent cover for covering surfaces of both said illumination and viewing windows; and a window glass that is attached to and covers said viewing window, said window glass having a flat front surface and a flat rear surface, said window glass having a diameter large enough so that a virtual image of an outer edge portion of said window glass, which is produced by single reflection from an inner side of an outer surface of said transparent cover, lies outside the visual field of said objective optical system, said illumination window being uncovered by said window glass.

2. A distal end part of an endoscope according to claim 1, wherein both said illuminating and viewing windows are disposed to face forwardly.

3. A distal end part of an endoscope according to claim 1, wherein said transparent cover is in close contact with a surface of said window glass.

4. A distal end part of an endoscope according to claim 1, wherein said transparent cover can be attached to and removed from said distal end part.

5. A distal end part of an endoscope according to claim 4, wherein said transparent cover is provided at a distal end of a sheath which is removably fitted over an insert part of said endoscope.

6. A distal end part of an endoscope according to claim 1, wherein said outer end portion of said window glass is chamfered.

7. A distal end part of an endoscope according to claim 1, comprising an aperture diaphragm located proximate said window glass.

8. A distal end part of an endoscope according to claim 7, wherein said objective optical system includes at least one objective lens, said aperture diaphragm being located between said at least one objective lens and said window glass.

* * * * *